United States Patent [19]

Hopkins

[11] 4,430,427

[45] Feb. 7, 1984

[54] RED ABSORBING COMBINATION OF ALCOHOL OXIDASE AND AN AZIDE COMPOUND

[75] Inventor: Thomas R. Hopkins, Bartlesville, Okla.

[73] Assignee: Phillips Petroleum Company, Bartlesville, Okla.

[21] Appl. No.: 203,923

[22] Filed: Nov. 4, 1980

[51] Int. Cl.³ .................. C12Q 1/26; C12N 9/02; C12N 9/04; C12N 9/96

[52] U.S. Cl. .................. 435/25; 435/188; 435/189; 435/190; 435/814; 435/815; 435/816

[58] Field of Search ............ 435/25, 4, 190, 188, 435/189, 174, 177, 180, 814, 815, 816

[56] References Cited

U.S. PATENT DOCUMENTS

| | | | |
|---|---|---|---|
| 3,627,640 | 12/1971 | Blumberg et al. | 435/815 X |
| 3,985,617 | 10/1976 | Yugari et al. | 435/180 X |
| 4,160,698 | 7/1979 | Miyairi et al. | 435/180 X |
| 4,250,254 | 2/1981 | Modrovich | 435/190 X |
| 4,250,261 | 2/1981 | Eggeling et al. | 435/25 |

OTHER PUBLICATIONS

Bringer, et al., Purification and Properties of Alcohol Oxidase from *Poria contigua*, Eur. J. Biochem. vol. 101, 11/79, (pp. 563–570).

*Primary Examiner*—David M. Nafe

[57] ABSTRACT

Combining active alcohol oxidase with sufficient amount of an azide compound has been found to form a red absorbing combination. Formation of the red absorbing combination enables determining the presence of active alcohol oxidase by adding the azide compound to a preparation and observing the resultant color. Additionally, alcohol oxidase may be purified by adding the azide compound to a preparation containing active alcohol oxidase in an amount effective to produce a red absorbing complex and separating the red absorbing complex from the preparation.

28 Claims, No Drawings

RED ABSORBING COMBINATION OF ALCOHOL OXIDASE AND AN AZIDE COMPOUND

FIELD OF THE INVENTION

The invention relates to enzymes. In one aspect of the invention relates to the isolation and purification of enzymes. In another aspect, the invention relates to combinations of enzymes with other compounds to form light absorbing associations.

BACKGROUND OF THE INVENTION

Biotechnology, dealing with the preparation and use of biological systems, living or nonliving, in industrial applications is a rapidly expanding area of technology. One area of biotechnology involves the industrial or technological use of enzyme preparations which can be preferred, for example, in preparative or analytical chemistry, because of the great specificity possessed by enzymes. Such an increased use of enzymes requires that large quantities of relatively pure enzymes be available.

One such enzyme having industrial utility in alcohol oxidase which can be used in analytical or preparative chemistry involving one or more of the compounds of the following equation catalyzed by alcohol oxidase:

$$ROH + O_2 \underset{}{\overset{A.O.}{\rightleftharpoons}} H_2O_2 + R'CHO$$

wherein the abreviation A.O. indicates that the reaction occurs in the presence of alcohol oxidase, R is the alkyl group of 1, 2, 3, or more carbon atoms and R' is hydrogen or an alkyl group having 1, 2, or more carbon atoms so that R' has 1 fewer carbon atoms than R.

In order to follow the isolation of a single protein, some quantitative method of protein estimation is essential. In the case of purification of enzymes or protein hormones, estimation of specific activity of the enzyme is usually used to follow purification of the enzyme.

Enzymes can generally be purified, among others, by procedures such as the following: (1) differential solubility; (2) specific precipitation; (3) column chromatography; (4) preparative electrophoresis; and/or (5) preparative ultracentrifugation.

Methods of preparing alcohol oxidase such as, for example, the following are known in the prior art.

Janssen and Ruelius, 151 Biochem. Biophys. Acta 317 (1968) describe a method for production of crystalline alcohol oxidase using fractional precipitation with polyethylene glycol.

Tani et al., 36 Agr. Biol. Chem. 68 (1972) describe a method for preparation of crystalline alcohol oxidase using ammonium sulfate precipitation, column chromatography, and crystallization with solid ammonium sulfate.

Fujii and Tonomura, 36 Agr. Biol. Chem. 2297 (1972) describe a method for production of crystalline alcohol oxidase using ammonium sulfate precipitation and column chromatography.

Baratti et al., XX Biotech. and Bioeng. 333 (1978) describe a method for preparing immobilized alcohol oxidase by adsorption on DEAE cellulose, sometimes preceded by ammonium sulfate precipitation.

Purification of enzymes or of other natural products is an empirical procedure and the various methods are largely the result of trial of various procedures and materials known in the art to be effective as well as trial of new procedures and materials. At each stage of purification, the enzyme preparation must typically be monitored for (specific) activity or by physical examination. Testing enzyme activities for specific activity is generally time consuming and a fast accurate way of following active alcohol oxidase being purified without tests for specific activity is therefore highly desirable.

Further, even after alcohol oxidase preparation is sufficiently purified for the use to which it will be put, it is highly desirable to have an indicator of enzyme activity which does not require a measurement or observation of specific activity. Such an indicator could be included as a small part of a large quantity of alcohol oxidase and used to indicate the quality, i.e., activity or inactivity of the enzyme.

An object of the invention is a method and composition of matter for determining the presence of active alcohol oxidase without the necessity for observation of specific activity. Other objects of the invention are methods for purifying and isolating alcohol oxidase. Yet other objects and advantages of the instant invention will be apparent to one skilled in the art from the following description and the claims.

SUMMARY OF THE INVENTION

According to the invention is a composition of matter comprising alcohol oxidase and an azide compound. Further according to the invention is a method of determining the presence of active alcohol oxidase by adding an azide compound, if such a compound is not present, and observing the resulting color. Further according to the invention is a method of purifying alcohol oxidase comprising making an enzyme preparation comprising alcohol oxidase, adding an azide compound to form a light absorbing combination with the alcohol oxidase, and separating the light absorbing combination from the rest of the enzyme preparation.

DETAILED DESCRIPTION OF THE INVENTION

According to the invention there is provided a composition of matter comprising an azide having the characteristic formula $R''(N_3)_x$, where $R''$ may be a metal atom, a hydrogen atom, the ammonium radical, a complex, and the like, and an enzyme preparation comprising alcohol oxidase.

As indicated, the azide can be any azide which combines with alcohol oxidase to produce a new specifically absorbing species. Preferred azides are the metal salts of azides, particularly the electropositive metal azides which are not explosive. Particularly preferred are metal azides selected from Group 1A of the Periodic Table according to Mendeleev, such as lithium azide, sodium azide, potassium azide, and the like.

The enzyme preparation comprising alcohol oxidase can be any suitable enzyme preparation comprising alcohol oxidase which catalyzes the following reaction (1)

$$CH_3OH + O_2 \underset{}{\overset{A.O.}{\rightleftharpoons}} HCHO + H_2O_2 \qquad (1)$$

Although reaction (1) appears to be the reaction catalyzed by the alcohol oxidase enzyme in living intact systems, the enzyme can also catalyze other oxidation-reduction type reactions representable by the following reaction (2) although the rate of catalysis may vary:

$$ROH + O_2 \underset{}{\overset{A.O.}{\rightleftharpoons}} R'CHO + H_2O_2 \qquad (2)$$

wherein R can be a methyl, ethyl, propyl, butyl, or allyl group and R' can be hydrogen, methyl, ethyl, propyl or vinyl group so that each R' group has one fewer carbon than a corresponding R group.

Alcohol oxidases capable of catalyzing this reaction can be isolated from methanol utilizing species of microorganisms when grown on a medium using methanol as a carbon and energy source. Suitable methanol utilizing microorganisms are methanol utilizing microorganisms selected from yeast and other fungi.

Suitable yeasts can include methanol utilizing species from the genera Candida, Hansenula, Torulopsis, Saccharomyces, Pichia, Debaryomyces, Lipomyces, Cryptococcus, Nematospora, and Brettanomyces. The preferred genera include Candida, Hansenula, Torulopsis, Pichia, and Saccharomyces. Examples of suitable species include methanol utilizing forms of:

| | |
|---|---|
| *Candida boidinii* | *Torulopsis bolmii* |
| *Candida mycoderma* | *Torulopsis versatilis* |
| *Candida utilis* | *Torulopsis glabrata* |
| *Candida stellatoidea* | *Torulopsis molishiana* |
| *Candida robusta* | *Torulopsis nemodendra* |
| *Candida claussenii* | *Torulopsis nitratophila* |
| *Candida rugosa* | *Torulopsis* |
| *Brettanomyces petrophilium* | *Pichia farinosa* |
| *Hansenula minuta* | *Pichia polymorpha* |
| *Hansenula saturnus* | *Pichia membranaefaciens* |
| *Hansenula californica* | *Pichia pinus* |
| *Hansenula mrakii* | *Pichia pastoris* |
| *Hansenula silvicola* | *Pichia trehalophila* |
| *Hansenula polymorpha* | *Saccharomyces cerevisiae* |
| *Hansenula wickerhamii* | *Saccharomyces fragilis* |
| *Hansenula capsulata* | *Saccharomyces rosei* |
| *Hansenula glucozyma* | *Saccharomyces acidifaciens* |
| *Hansenula henricii* | *Saccharomyces elegans* |
| *Hansenula nonfermentans* | *Saccharomyces rouxii* |
| *Hansenula philodendra* | *Saccharomyces lactis* |
| *Kloeckera spp.* | *Saccharomyces fractum* |
| *Torulopsis candida* | |

Suitable fungi include methanol utilizing species from the genera Aspergillus, Monilia, Rhizopus, Penicillium, Mucor, Alternaria and Helminthosporium.

Examples of suitable species of fungi include methanol utilizing forms of:

| | |
|---|---|
| *Aspergillus niger* | *Penicillium italicum* |
| *Aspergillus glaucus* | *Polyporus obtusus* |
| *Aspergillus flavus* | *Radulum casearium* |
| *Aspergillus terreus* | *Rhizopus nigricans* |
| *Aspergillus itconicus* | *Rhizopus oryzae* |
| *Penicillium notatum* | *Rhizopus delemar* |
| *Penicillium chrysogenum* | *Rhizopus arrhizus* |
| *Penicillium glaucum* | *Rhizopus stolonifer* |
| *Penicillium griseofulvum* | *Mucor mucedo* |
| *Penicillium expansum* | *Mucor genevensis* |
| *Penicillium digitatum* | |

The fermentation process for the growth of the alcohol oxidase producing microorganisms can be any fermentation process utilizing methanol as a carbon and energy source and which is effective for the production of alcohol oxidase. Clearly, these processes include those which use methanol as the sole carbon and energy source. However, the process can also include other carbon and energy sources if the presence of the other carbon and energy sources do not inhibit or repress production of alcohol oxidase. German Auslegeschrift DE No. 28 30 327, for example, describes production of alcohol oxidase in a medium comprising nonalcohol oxidase repressing substrate such as glycerin, sorbite, or xylose, in addition to methanol. Fermentation processes utilizing generally methanol are now well described in the art and are within the artisan's skill.

Particularly preferred fermentation processes are high cell density fermentations such as hereinafter described in Example I because such fermentation processes which can produce a cell density of 100 grams per liter or even higher facilitate the production and isolation of alcohol oxidase in large quantities.

Particularly preferred microorganisms for production of alcohol oxidase are methanol utilizing yeasts of genera Candida, Pichia, Hansenula, and Torulopsis. Presently most preferred are methanol utilizing Pichia yeasts including
*Pichia pastoris*
*Pichia pinus*
*Pichia trehalophila*
*Pichia molishiana*

Two exemplary strains of suitable yeasts of genus *Pichia pastoris* have been deposited with the United States Department of Agriculture, Agriculture Research Service, Northern Regional Research laboratories of Peoria, Illinois, and have received the numerical designations NRRL Y-11430 and Y-11431.

These strains of *Pichia pastoris* are presently most preferred because the strains are capable of high cell density growth as described below in Example I and can further produce alcohol oxidase which is easily crystallized as further described below in Example I.

The method for making the enzyme preparation comprising alcohol oxidase can be any suitable method. For example, a preparation comprising crude alcohol oxidase can be prepared by disrupting the microbial cells, by, for example, ultrasonication, grinding with a mortar and pestle, milling with glass beads, and the like. The cell free extract can be obtained by centrifugation, filtration, and the like to remove cellular debris. The cell free extract can be fractionated with, for example, ammonium sulfate, polyethylene glycol, and the like followed by column chromatography, dialysis, and the like as are known in the art, to produce a purified form of the enzyme. Preferably the cell free extract is treated by dialysis by a method described below in Example I to produce crystalline alcohol oxidase.

The azide compound is added to the alcohol oxidase preparation in an amount effective to produce an absorbance change preferably observed at 522 nm (broadly observed at 300–650 nm) in the presence of active enzyme. The amount of azide to be added can be readily determined by the artisan. Broadly, however, the azide can range from about 1 mole azide ($N_3^-$) per mole enzyme to about $5 \times 10^7$ moles azide ($N_3^-$) per mole enzyme where the lower limit is an amount effective to give a detectable change in absorbance at, for example, 522 nanometers and the upper limit is determined by solubility of the azide ($N_3^-$) in water. Preferably, the azide is present in an amount in excess of that required to saturate the binding sites of the enzyme, i.e., above about 8 moles azide per mole enzyme as shown in Example XII, for maximum color development. Most preferably the azide is present in an amount in the range of about 10 moles azide to about 2000 moles azide per mole enzyme.

The amount of azide can also be expressed in weight/weight terms if the molecular weight of the enzyme is known. For the alcohol oxidase isolated from *Pichia pastoris* described herein and having an estimated molecular weight of about 625,000, the azide can be added broadly in an amount in the range of about 0.07 mg to about 80,000 mg per gram alcohol oxidase, more preferably above about 0.1 mg per gram alcohol oxidase, most preferably in the range of about 0.7 mg to about 135 mg azide per gram alcohol oxidase.

The amount of azide to be added can also be expressed in terms of the enzyme activity and this may be particularly convenient when dealing with crude preparations. In the instance of the alcohol oxidase having a specific activity of 10–12 E.U. (enzyme units) per milligram of alcohol oxidase, the azide can be broadly in the range of from about $7 \times 10^{-6}$ mg to about 8 mg azide ($N_3^-$) per Enzyme Unit, preferably above about $7 \times 10^{-5}$ mg azide ($N_3^-$)/EU, most preferably in the range of about $7 \times 10^{-4}$ mg azide ($N_3^-$/EU to about $1.35 \times 10^{-2}$ mg azide ($N_3^-$)/EU. By an enzyme unit (EU) as used herein is meant the amount of enzyme required to oxidize 1 μmole MeOH in one minute. Correlative ranges for other alcohol oxidases having other specific activities can be readily determined by the artisan.

The resulting color can be observed by any suitable means, optically (by eye) or instrumentally or both. When color is instrumentally followed it can be readily observed at 522 nm, broadly 300–650 nm. The instruments used can be any suitable instrument for determining transmittance or absorbance of light at the frequencies concerned.

As indicated, the invention also comprises methods of purifying alcohol oxidase comprising preparing an enzyme preparation comprising alcohol oxidase, adding an azide compound effective to form a light absorbing combination with the alcohol oxidase, and separating the light absorbing combination from the rest of the enzyme preparation. The enzyme preparation can be prepared by any suitable preparative method such as, for example, those set forth above. The azide can be added also as set forth above. The separating step can use any suitable procedure for separating the red absorbing combination from the other components present in the crude preparation. The red absorbing combination can be removed, for example, (1) by differential solubility using, for example, ammonium sulfate or polyethylene glycol; (2) by specific precipitation; (3) by column chromatography; (4) by preparative electrophoresis; (5) by preparative ultracentrifugation; (6) by any other enzyme preparative method known to the artisan; or (7) by dialysis to crystallization as herein described. Other suitable methods can also be employed by the artisan. Particularly preferred are those methods such as column chromatography, electrophoresis and the like where the color absorbing complex can facilitate recovery of purified protein.

To further illustrate the invention, the following examples are provided.

EXAMPLE 1

In a continuous aerobic fermentation process, methanol and an aqueous mineral salts medium in a volume ratio of about 40 to 60, respectively, were fed individually to a fermenter, innoculated with the yeast species *Pichia pastoris* NRRL Y-11430, at a rate so that methanol is the growth-limiting factor. The fermenter was a 1500-liter foam-filled fermenter with a liquid volume of about 610 liters, with automatic pH, temperature, and level control. Agitation was provided by two conventional paddle-type turbines driven at 1000 rpm. The aeration rate was about 4 volumes of air (at about 38 psig and about 25° C.) per volume of ferment in the fermenter per minute. Anhydrous ammonia was added at such a rate as to maintain the pH of the fermentation mixture at about 3.5.

The aqueous mineral salts medium was prepared by mixing, with each liter of tap water, 15.86 mL 75 percent $H_3PO_4$, 9.53 g $K_2SO_4$, 7.8 g $MgSO_4.7H_2O$, 0.6 g $CaCl_2.2H_2O$, and 2.6 g 85 percent KOH. The trace mineral solution plus biotin was fed separately via the methanol stream at a rate of 10 mL per liter of methanol. The trace mineral solution plus biotin was prepared by mixing 780 mL of a trace mineral solution, 20 mL water, 200 mL methanol and 0.032 g biotin.

The trace mineral solution was prepared by mixing, for each liter of solution, 65 g $FeSO_4.7H_2O$, 20 g $ZnSO_4.7H_2O$, 3.0 g $MnSO_4.H_2O$, 6.0 g $CuSO_4.5H_2O$, 5.0 mL conc. $H_2SO_4$, and sufficient deionized water to make 1 liter of solution.

The aqueous mineral salts medium was fed at a rate of 31.5 liters per hour and the methanol at a rate of 21 liters per hour.

The fermentation was conducted at about 30° C. and about 38 psig pressure, with a retention time of 11.6 hours.

For analytical purposes, the resulting yeast cells were separated from the fermentation effluent (ferment) by centrifugation, washed by suspension in water and recentrifugation, dried overnight at 100° C., and weighed. On a dried basis, the yield of yeast cells typically was about 40.6 g per 100 g of methanol fed. The cell density typically was about 128.4 g of cells per liter of fermenter effluent. The total solids content of the ferment typically was about 134.7 g per liter, cells plus dissolved solids. A portion of the fermenter effluent was frozen and stored.

Fermentation of *Pichia pastoris* NRRL Y-11430 was carried out by a method of which that set forth above is typical. A portion of the fermenter effluent was removed and adjusted to pH 7.5 with ammonium hydroxide, and was homogenized on a Dyno-Mill Model KDL using a 0.6 liter vessel in a continuous operation at 30° C. using belt combination #3 and a flow of 20–30 mL/hr. The beads in the mill were lead free glass beads with a diameter of 0.3–0.5 mm. The resulting homogenate was centrifuged at 5° C. and 20,000×g for 30 minutes to yield a cell-free supernatant. The cell-free supernatant enzyme activity measured by dye-peroxidase method described below was about 330 EU/mL. The supernatant was stored frozen for future use. This describes the preparation of crude yeast homogenate.

Six 130 mL portions of the supernatant were placed in cellulose acetate dialysis bags and dialyzed at 5° C. against about 8 liters of distilled water. After 4 days, the aqueous phase of each bag was decanted. The solids remaining in the bags consisted of two types of solid. The thin upper white layer was carefully removed and discarded. The bottom solid was brown-yellow and was crystalline alcohol oxidase. A portion of the crystalline alcohol oxidase was dissolved in distilled water (about 10 times the volume of the solid) and an assay by the dye-peroxidase method showed an activity of 94 EU/mL. The specific activity of the alcohol oxidase was 10.4 EU/mg of protein.

A sample of the solid alcohol oxidase was examined by SDS gel electrophoresis and a single band was observed indicating a homogeneously pure enzyme. A comparison of electrophoretic mobility with those of proteins having known molecular weight indicates a subunit molecular weight of about 72,000±3000 (estimated). This describes the preparation of pure yeast alcohol oxidase from *Pichia pastoris*.

The alcohol oxidase activity for reaction with methanol was determined by the following assay procedure (dye-peroxidase method). A dye-buffer mixture was prepared by mixing 0.1 mL of an o-dianisidine solution (1 weight % o-dianisidine in water) with 12 mL of aerated 0.1 M sodium phosphate buffer (pH 7.5). The assay mixture was prepared with 2.5 mL of the dye-buffer mixture, 50 μL of methanol, 10 μL of a peroxidase solution (1 mg of horse-radish peroxidase-Sigma, Type II), and 25 μL of the alcohol oxidase solution. The assay mixture was maintained at 25° C. in a 4×1×1 cm cuvette and the increase in absorbance by the dye at 460 nm was recorded for 2 to 4 minutes. The enzyme activity was calculated by $$\text{Activity } (\mu \text{ mole/min/mL or Enzyme Units/mL}) = \frac{\Delta A}{\min} \times 11.5$$

wherein 11.5 is a factor based on a standard curve prepared with known aliquots of $H_2O_2$ and $\Delta A$ is the change in absorbance during the experimental interval.

EXAMPLE II

Fermentation of *Hansenula polymorpha*

A continuous aerobic fermentation process was conducted in the fermenter as described in Example I, this time inoculated with the yeast species *Hanenula polymorpha* Culture 21-3 deposited as NRRL Y-11432. To the fermenter was fed a mixture of methanol and aqueous mineral salts medium containing 300 mL methanol per liter total solution. The stirred fermentation mixture was aerated by passing into the fermenter 2 volumes (at about atmospheric pressure and about 25° C.) per volume of ferment per minute of air supplemented with and including sufficient oxygen to maintain in the fermentation mixture an amount of dissolved oxygen equal to about 20 percent of that which would be dissolved in the fermentation mixture saturated with air at atmospheric pressure and about 38° C.

Aqueous ammonium hydroxide (from 2 parts concentrated ammonium hydroxide and 1 part deionized water, by volume) was added at a rate to maintain the pH of the fermentation mixture at 3.7 to 4.1.

The mixture of methanol and aqueous mineral salts medium was prepared by mixing, for each liter of solution, 300 mL methanol, 6 mL 85 percent $H_3PO_4$, 3 g KCl, 4.5 g $MgSO_4.7H_2O$, 0.6 g $CaCl_2.2H_2O$, 0.3 g NaCl, 10 mL of trace mineral solution A as described below, 10 mL of trace mineral solution B as described below, 4 mL of the biotin-thiamine hydrochloride solution described below, 4 drops of antifoam agent, and sufficient deionized water to make 1 liter of solution.

Trace mineral solution A was prepared by mixing, for each liter of solution, 4.8 g $FeCl_3.6H_2O$, 2.0 g $ZnSO_4.7H_2O$, 0.02 g $H_3BO_3$, 0.20 g $Na_2MoO_4$, and sufficient deionized water to make 1 liter of solution.

Trace mineral solution B was prepared by mixing, for each liter of solution, 2.0 g $FeCl_3.6H_2O$, 2.0 g $ZnSO_4.7H_2O$, 0.3 g $MnSO_4.H_2O$, 0.6 g $CuSO_4.5H_2O$, 2 ml conc. $H_2SO_4$, and sufficient deionized water to make 1 liter of solution.

The biotin-thiamine hydrochloride solution was prepared by mixing 2 mg biotin, 200 mg thiamine hydrochloride, and 50 mL deionized water.

The fermentation was conducted at about 38° C. and about atmospheric pressure, with a retention time of 5.66 hours.

Yeast cells were separated from the fermentation effluent, washed, and dried as in Example I. On a dried basis, the yeast cells were produced in a yield of 31.0 g per 100 g of methanol fed, the cell density being at 73.3 g of cells per liter of effluent.

EXAMPLE III

Development of Red Color with Pichia Alcohol Oxidase

Four one mL samples of purified enzyme solution (prepared as described in Example I) which contain 1-50 mg of enzyme (limited by enzyme solubility at high concentration and detectability of color at low concentration) are mixed with a few crystals (qualitative, about 1 mg) of $NaN_3$, NaCN, or KSCN. The samples are allowed to stand at room temperature for 15 minutes. Color and enzyme activity are monitored at that time. The results are shown in Table 3:

TABLE 3

| Run | Compound Added | EU/mL* at 15 min. | Color at 15 min. |
|---|---|---|---|
| 1 | None | 70 | None |
| 2 | $NaN_3$ | 75 | Red immediately |
| 3 | NaCN | 65 | None |
| 4 | KSCN | 25 | None initially - becomes slightly pink later |

*measured as described in Example I.

This example demonstrates the color-forming interaction of alcohol oxidase with sodium azide. Color is observed within a few seconds, and persists.

EXAMPLE IV

Development of Red Color with *Hansenula polymorpha* Alcohol Oxidase

Fermentation effluent from the aerobic fermentation of *Hansenula polymorpha* (prepared as described in Example II) was adjusted to pH 7.5 with concentrated ammonium hydroxide. Sample was homogenized and disrupted on a Dyno-Mill Model KDL using a 0.6 L vessel in a continuous operation at 30° C. using belt combination #3 and a flow of 20-30 mL/hr. The beads were lead-free glass beads with a diameter of 0.3-0.5 mm. The resulting homogenate was centrifuged for 20 minutes at 10,000×g to yield a cell-free supernatant. The material thus prepared exhibited a specific activity of 4.9 (when analyzed by the dye-peroxidase method described in Example I), and gave a red color when treated with sodium azide as follows:

One mL of this crude enzyme preparation was mixed with a few crystals (qualitative—one mg) of $NaN_3$ is a test tube. Red color forms upon mixing.

This example demonstrates that crude cell free extracts of alcohol oxidase from *Hansenula polymorpha* form a red color in the presence of $NaN_3$.

EXAMPLE V

Development of Red Color with purified Hansenula Alcohol Oxidase

*Hansenula polymorpha* cell homogenate (prepared as described in Example II) (150 mL) is dialyzed against water to remove salts and other low molecular weight materials, then subjected to sequential protein precipitation by treatment with increasing amounts of polyethylene glycol (PEG) with a molecular weight of 6000. Sample is allowed to settle for 15 minutes after addition of PEG, then centrifuged at 12,000×g for 30 minutes. The resultant pellet is resuspended in 150 mL standard phosphate buffer (pH −7.5) and assayed for alcohol oxidase activity as described in Example I and color formation upon addition of sodium azide crystals. The supernatant liquid is treated with additional PEG for 15 minutes, and so on, as above. The results are shown in Table 5A:

TABLE 5A

| Cumulative wt. % PEG Added | Color | Alcohol Oxidase Activity (EU/mL) |
|---|---|---|
| 0.7 | Clear | 1 |
| 2.0 | Red | 132 |
| 5.0 | Red | 161 |
| 10.0 | Yellow-green | 3.9 |
| Final supernatant | Yellow | <0.5 |

The same treatment was repeated with Pichia cell homogenate (prepared as described in Example I). The results are shown in Table 5B:

TABLE 5B

| Cumulative wt. % PEG Added | Color | Alcohol Oxidase Activity (EU/mL) |
|---|---|---|
| 0.7 | Clear | 2 |
| 2.0 | Clear | 4 |
| 5.0 | Orange-red | 69 |
| 10.0 | Red | 169 |
| Final supernatant | Yellow | 0 |

This example demonstrates that a qualitative correlation exists between alcohol oxidase activity in different fractions and the formation of red color in the presence of azide ion.

EXAMPLE VI

Dependence of Red Color on Enzyme Activity

A red enzyme-azide combination was prepared according to the procedure detailed in Example III. When this sample is heated to boiling over a laboratory burner the red solution becomes yellow. The solution remains yellow upon cooling back to room temperature.

This example demonstrates that treatment to denature the enzyme alcohol oxidase to produce inactive alcohol oxidase causes loss of the enzyme-azide red color.

EXAMPLE VIIA

Dependence of Red Color on Oxidation State of Cofactor

Into an anaerobic cuvette is placed 2.5 mL of purified Pichia alcohol oxidase (purified as described in Example I) with a few crystals of sodium azide (about 1 mg). The absorption spectrum is scanned from 350–550 nm, with particular attention to absorption maxima at 370–380 nm and 450–470 nm. This spectral region includes the absorption bands characteristic of the oxidized form of flavine adenine dinucleotide (FAD) cofactor (Scan 1). An excess of oxygen-free ethanol is then injected into the cuvette, and the sample is again scanned from 350–550 nm (Scan 2). The optical densities of the resultant absorption maxima at about 380 and 450 nm are tabulated below. There is a substantial decrease in the absorption at the wavelengths characteristic of oxidized cofactor, FAD. The color of the sample changes from red to pale yellow upon introduction of ethanol. When oxygen is reintroduced to the enzyme-alcohol mixture by opening the cuvette to the air, the red color returns. The absorption spectrum is again recorded between 350–550 nm (Scan 3). The data are tabulated in Table 7A below.

TABLE 7A

| Scan | Azide | Optical Density 370 λmax | Optical Density 455 λmax | Cofactor Redox State | Color |
|---|---|---|---|---|---|
| 1 | Yes | 0.57 | 0.47 | Oxidized | Red |
| 2 | Yes | 0.41 | 0.19 | Reduced | Yellow |
| 3 | Yes | 0.62 | 0.49 | Oxidized | Red |

The results of this example demonstrate that enzyme in the reduced state (FADH$_2$) does not give a red color in the presence of azide ion, whereas enzyme in the oxidized state (FAD) does give a red color.

EXAMPLE VIIB

Dependence of Color Formation on Oxidation State of Cofactor

Three mL of a purified Pichia alcohol oxidase solution containing about 7 mg/mL enzyme are placed in a cuvette with a 1 cm. pathlength. Sample is then scanned from 350–550 nm (Scan 1). To the sample, in the absence of air, is added 1 μL ethanol. Sample is then scanned again (Scan 2). Maintaining the sample in the absence of air, several crystals (about 1 mg) of sodium azide are mixed with the alcohol-enzyme solution, which is scanned from 350–550 nm again (Scan 3). The cuvette is then opened to the air and stirred. Red color appears for a few seconds, but does not persist for sufficient time to allow a complete scan. Sample simply reverts to the pale yellow observed before air is introduced. Scan 4 records the sample after exposure to air. The results are tabulated in Table 7B.

TABLE 7B

| Scan | Azide | Optical Density 370 λmax | Optical Density 455 λmax | Cofactor Redox State | Color |
|---|---|---|---|---|---|
| 1 | No | .72 | .58 | Oxidized | Yellow |
| 2 | No | .61 | .33 | Reduced | Yellow |
| 3 | Yes | .61 | .33 | Reduced | Yellow |
| 4 | Yes | .62 | .34 | Oxidized (when agitated) | Yellow (red when agitated) |

This example demonstrates that a red enzyme-azide combination does not form in the presence of reduced co-factor. When oxygen was admitted by agitation, the red color returns. In this experiment, a large excess of ethanol was present which caused the cofactor to return to the reduced state. Continual agitation to provide sufficient oxygen to the enzyme was not practical in the cuvette.

EXAMPLE VIIC

The same procedure as Example VIIB was then repeated, except only enough ethanol was added to cause reduction of cofactor. This was done by shaking a cuvette equipped with a side arm containing ethanol and three mL of fresh purified enzyme solution in the cuvette so that ethanol vapor could diffuse into the enzyme solution. Scan 1 represents untreated enzyme solution; scan 2 is the ethanol treated sample. The ethanol containing side arm is replaced with a sodium azide containing side arm. The enzyme solution and sodium azide are then mixed, and solution is scanned (Scan 3). Note that some air is introduced in the process of transferring side arms, which may have affected the result of Scan 3. Sample is then opened to the air and scanned once more (Scan 4). The results are tabulated in Table 7C.

TABLE 7C

| Scan | Azide | Optical Density 370 λmax | 455 λmax | Cofactor Redox State | Color |
|---|---|---|---|---|---|
| 1 | No | 0.68 | 0.55 | Oxidized | Yellow |
| 2 | No | 0.59 | 0.36 | Reduced | Yellow |
| 3 | Yes | 0.64 | 0.42 | Reduced | Yellow |
| 4 | Yes | 0.74 | 0.56 | Oxidized | Red |

This example demonstrates that the red color of the enzyme-azide combination returns when air (oxygen) is reintroduced to the enzyme having reduced cofactor.

EXAMPLE VIII

Inhibition of Methanol Conversion by Azide Ion ($N_3^-$)

A series of solutions were prepared by combining 3.9 mL standard phosphate buffer (pH 7.5) having $NaN_3$ (g/l) as set forth in Table 8, 15 μL saturated solution of purified Pichia alcohol oxidase, and 50 μL methanol solution (% V/V in $H_2O$). Reaction velocity V (rate of methanol oxidation in the presence of alcohol oxidase) was monitored by a dissolved oxygen probe by following oxygen consumption (oxygen is consumed as alcohol substrate, S, is oxidized in the presence of the enzyme). The results are tabulated in Table 8.

TABLE 8

| $NaN_3$ (g/l) | [S] (MeOH conc. M) | 1/V |
|---|---|---|
| 0 | .016 | .0294 |
|  | .008 | .0328 |
|  | .004 | .0355 |
|  | .002 | .0379 |
|  | .001 | .0524 |
|  | .0005 | .0752 |
|  | .00025 | .1176 |
|  | .000125 | .1667 |
|  | .0000625 | .4348 |
|  | .00003125 | .6667 |
| .0001 | .016 | .04 |
|  | .004 | .0488 |
| .0002 | .016 | .0377 |
|  | .008 | .0455 |
|  | .004 | .0588 |
|  | .002 | .0725 |
|  | .001 | .1429 |
|  | .0005 | .2632 |
| .0005 | .016 | .0602 |
|  | .008 | .0813 |
|  | .004 | .1111 |
|  | .002 | .1667 |
|  | .001 | .4 |
|  | .0005 | .625 |
| .001 | .016 | .0645 |
|  | .008 | .111 |

TABLE 8-continued

| $NaN_3$ (g/l) | [S] (MeOH conc. M) | 1/V |
|---|---|---|
|  | .004 | .1667 |
|  | .002 | .333 |
|  | .001 | 1 |

Plots of the above data as 1/V vs 1/[S] for various inhibitor ($NaN_3$) concentrations are linear, but do not intersect at a single point. The plot indicates a linear, mixed-type inhibition, implying a combination of competitive and noncompetitive inhibition. This suggests that inhibitor ($NaN_3$) and substrate (methanol) may bind to the enzyme at different sites. The binding constants for methanol substrate, $K_S$, and for $NaN_3$ inhibitor, $K_i$, have been estimated from these plots to be $6 \times 10^{-4}$ and $6 \times 10^{-6}$, respectively.

EXAMPLE IX

Use of Red Color as a Qualitative Measure of Alcohol Oxidase

Whole Pichia yeast cells (prepared as described in Example I) are treated as described below in attempts to release alcohol oxidase enzyme from the cells. The cell broth is adjusted to pH 7.5 with concentrated ammonium hydroxide and then 30 mL aliquots are treated with xylene+sodium dodecyl sulfate (SDS). This mixture is incubated as indicated, then centrifuged for 15 minutes at 20,000×g. The supernatant is assayed for alcohol oxidase activity by the method described in Example I, and color formation by the method described in Example III. The results are tabulated in Table 9.

TABLE 9

| Run | Reagent Treatment, (mL xylene, mg SDS) | Incubation Time | Temperature | Enzyme Activity (EU/mL) | Red Color |
|---|---|---|---|---|---|
| 1 | 0.1    30 | 2 days | 4° C. | .17 | No |
| 2 | 0.6    30 | 2 days | 4° C. | .17 | No |
| 3 | 2    30 | 2 days | 4° C. | .55 | No |
| 4 | .6    100 | 2 days | 4° C. | .27 | No |
| 5 | .6    3 | 2 days | 4° C. | .36 | No |
| 6 | .6    30 | 1 day | 4° C. | .15 | No |
| 7 | .6    30 | 1 week | 4° C. | 3.45 | No |
| 8 | .6    30 | 2 days | 25° C. | 125.4 | Yes |

Since the specific activity of Pichia pastoris alcohol oxidase is known to be 10–12 EU/mg (see Example I), the above data indicate a lower limit of about 0.3 mg alcohol oxidase/mL for visual detection (by eye) of alcohol oxidase by red color formation in the presence of sodium azide.

EXAMPLE X

Qualitative Means of Determining Activity

In a typical application of the red complex of alcohol oxidase-sodium azide, Pichia alcohol oxidase is tested for denaturation by a variety of inorganic salts, as described below. A few drops of crude enzyme (crude homogenate prepared as described in Example I) are placed on a spot plate. Then, sufficient salt crystals were added to produce a saturated solution. Samples were assayed 1–2 minutes later for color formation and for enzyme activity as described in Example I. The results are tabulated in Table X.

TABLE X

| Added Salt | Color Yellow | Color Yellow-Pink | Color Red | Relative Enz. Act. |
|---|---|---|---|---|
| LiCl | X | | | 0 |
| NaCl | X | | | 1 |
| KCl | | X | | 2 |
| MgCl$_2$ | X | | | 0 |
| NaH$_2$PO$_4$ | X | | | 0 |
| KH$_2$PO$_4$ | X | | | 0 |
| KH$_2$PO$_4$ | | | X | 3 |
| NaAc | | X | | 4 |
| Na$_2$HPO$_4$ | | X | | 4 |

This example demonstrates that pink or red color formation correlates well with enzyme activity as measured by independent means.

EXAMPLE XI

Quantative Determination of Enzyme

A solution of Pichi alcohol oxidase, purified as described in Example I, was prepared with a concentration of about 20 mg/mL in water. A series of 2-fold dilutions of this initial solution was then prepared. Each sample was analyzed for alcohol oxidase activity by the method described in Example I, and the optical density at about 520 nm was measured in a cuvette having a 1 cm pathlength. Several crystals of NaN$_3$ are added to each sample, and the optical density of resulting red solutions are measured again. The results are tabulated in Table XI.

TABLE XI

| Sample | EU/mL | OD | OD (after N$_3$) | ΔOD |
|---|---|---|---|---|
| 1 | 216.2 | .369 | 1.072 | .705 |
| 2 | 86.9 | .187 | .547 | .360 |
| 3 | 48.3 | .093 | .277 | .184 |
| 4 | 24.2 | .048 | .146 | .098 |

A plot of enzyme activity (EU/mL) vs ΔOD gives a generally straight line with a slope of about 0.04 ΔOD mL/mg.

This example demonstrates that one can quantitatively estimate the enzyme activity of a given preparation by measuring the optical density of an alcohol oxidase containing solution at about 520 nm before and after NaN$_3$ addition.

EXAMPLE XII

Determination of the Number of Sodium Azide Binding Sites 3 mL of purified enzyme containing 3 mg/mL enzyme (crystallized as described in Example I) were placed in a 1-cm quartz cuvette. The solution was scanned from 350-550 nm. This scan was repeated several times following the addition of sodium azide in incremental amounts, as set forth in Table 12:

TABLE 12

| μL Added 1 × 10$^{-3}$ M NaN$_3$ | Moles N$_3^-$/Moles Emzyme | Φ |
|---|---|---|
| 5 | .38 | .062 |
| 5 | .77 | .105 |
| 5 | 1.15 | .167 |
| 5 | 1.54 | .207 |
| 5 | 1.92 | .259 |
| 5 | 2.31 | .309 |
| 10 | 3.02 | .407 |
| 10 | 3.85 | .475 |
| 10 | 4.61 | .525 |
| 10 | 5.38 | .580 |
| 10 | 6.25 | .630 |
| 10 | 6.92 | .679 |
| Excess (solid crystals) | — | 1.000 | where $$\Phi = \frac{\Delta A_{522}}{\Delta A_{522}^{max}} = \text{fractional saturation,}$$

$\Delta A_{522}$ = change in absorbance at 522 nm upon NaN$_3$ addition, and $\Delta A_{522}^{max}$ = total change in absorbance at 522 nm upon saturation of enzyme solution with NaN$_3$.

These data are plotted as described by Brewer, Pesce, and Ashworth in "Experimental Techniques in Biochemistry" (Prentice-Hall, NJ, 1974) on pp. 248-9. The plot of fractional saturation, Φ, vs the ratio of ligand (N$_3^-$) concentration in moles to enzyme concentration comprises in moles two linear segments. Extrapolation of the stoichiometric line (where Φ = [N$_3^-$]/[Alcohol Oxidase]) to the baseline gives a value of 7.6 moles of azide per mole of enzyme.

The enzyme monomer molecular weight has been determined by polyacrylamide gel electrophoresis in the presence of sodium dodecyl sulfate to be 72,000 ± 3000 (estimated). The oligomer molecular weight, as determined by sedimentation diffusion, is found to be 625,000 ± 25,000 (estimated). Therefore, it is viewed as likely that the alcohol oxidase enzyme comprises 8 identical subunits.

Since about 7.6 moles of azide were found to bind with each mole of enzyme, this example suggests, within experimental error, that one azide molecule binds to each alcohol oxidase subunit.

As thus set forth above in illustrative embodiments and examples, it has been found that active alcohol oxidase changes color upon addition of azide compounds. The color changes are characteristic of the state of the enzyme and a red color is characteristic of active enzyme and is not characteristic of inactive enzyme. This unique color marker makes purification and visual estimation of activity and enzyme concentration very convenient. The invention is not to be limited by the illustrative embodiments and examples herein provided, however, but by the claims appended hereto.

That which is claimed is:

1. A composition of matter comprising active alcohol oxidase; and
    an azide compound selected from the group of compounds having the formula R"(N$_3$)$_x$ wherein R" is a metal atom, a hydrogen atom, or the ammonium radical, and N$_3$ is the moiety N=N=N,
    the azide compound being present in an amount effective to form a red absorbing combination with active alcohol oxidase.

2. A composition as in claim 1 wherein:
    the azide is selected from the group consisting of azide salts of electropositive metals.

3. A composition as in claim 1 wherein:
    the azide is present in an amount in the range of about 1 mole azide/mole alcohol oxidase to about 5.0 × 10$^7$ moles azide/mole alcohol oxidase.

4. A composition as in claim 1 wherein:

the azide is present in an amount in the range of about 8 moles azide/mole alcohol oxidase to about $5.0 \times 10^7$ moles azide/mole alcohol oxidase.

5. A composition as in claim 1 wherein:
the azide is present in an amount in the range of about 10 moles azide/mole alcohol oxidase to about 2000 moles azide/mole alcohol oxidase.

6. A composition as in claim 1 wherein:
the alcohol oxidase is isolated from genus Pichia; and
the azide is present in an amount in the range of about 0.07 mg azide/gram alcohol oxidase to about 80,000 mg azide/gram alcohol oxidase.

7. A composition as in claim 1 wherein:
the alcohol oxidase is isolated from genus Pichia; and
the azide is present in an amount in the range of about 0.1 mg azide/gram alcohol oxidase to about 80,000 mg azide/gram alcohol oxidase.

8. A composition as in claim 1 wherein:
the alcohol oxidase is isolated from genus Pichia; and
the azide is present in an amount in the range of about 0.7 mg azide/gram alcohol oxidase to about 135 mg azide/gram alcohol oxidase.

9. A composition as in claim 1 wherein:
the alcohol oxidase has a specific activity in the range of about 10-12 Enzyme Units per mg protein; and
the azide is present in an amount in the range of about $7 \times 10_6^-$ mg azide ($N_3$)/Enzyme Unit to about 8 mg azide ($N_3$)/Enzyme Unit.

10. A composition as in claim 1 wherein:
the alcohol oxidase has a specific activity in the range of about 10-12 Enzyme Units per mg protein; and
the azide is present in an amount in the range of about $7 \times 10^{-5}$ mg azide ($N_3$)/Enzyme Unit to about 8 mg azide ($N_3$)/Enzyme Unit.

11. A composition as in claim 1 wherein:
the alcohol oxidase has a specific activity in the range of about 10-12 Enzyme Units per mg protein; and
the azide is present in an amount in the range of about $7 \times 10^{-4}$ mg azide ($N_3$)/Enzyme Unit to about $1.35 \times 10^{-2}$ mg azide ($N_3$)/Enzyme Unit.

12. A method of purifying an active alcohol oxidase comprising:
adding an azide compound selected from the group of compounds having the formula $R''(N_3)_x$ wherein $R''$ is a metal atom, a hydrogen atom, or the ammonium radical, and $N_3$ is the moiety $N=N=N$ to a preparation comprising the active alcohol oxidase in an amount effective for producing a red absorbing complex; and separating the red absorbing complex from the preparation.

13. A method as in claim 12 wherein adding an azide comprises:
adding an amount of sodium azide in the range of about 1 mole azide/mole alcohol oxidase to about $5.0 \times 10^7$ moles azide/mole alcohol oxidase.

14. A method as in claim 12 wherein adding an azide comprises:
adding an amount of sodium azide in the range of about 8 moles azide/mole alcohol oxidase to about $5.0 \times 10^7$ moles azide/mole alcohol oxidase.

15. A method as in claim 12 wherein adding an azide comprises:
adding an amount of sodium azide in the range of about 10 moles azide/mole alcohol oxidase to about 2000 moles azide/mole alcohol oxidase.

16. A method as in claim 12 wherein adding an azide comprises:
adding an amount of sodium azide in the range of about 0.07 mg azide/gram alcohol oxidase to about 80,000 mg azide/gram alcohol oxidase; and wherein
the alcohol oxidase is isolated from genus Pichia.

17. A method as in claim 12 wherein adding an azide comprises:
adding an amount of sodium azide in the range of about 0.1 mg azide/gram alcohol oxidase to about 80,000 mg azide/gram alcohol oxidase; and wherein
the alcohol oxidase is isolated from genus Pichia.

18. A method as in claim 12 wherein adding an azide comprises:
adding an amount of sodium azide in the range of about 0.7 mg azide/gram alcohol oxidase to about 135 mg azide/gram alcohol oxidase; and wherein
the alcohol oxidase is isolated from genus Pichia.

19. A method as in claim 12 wherein adding an azide comprises:
adding an amount of sodium azide in the range of about $7 \times 10^{-6}$ mg azide ($N_3$)/Enzyme Unit to about 8 mg azide ($N_3$)/Enzyme Unit; and wherein
the alcohol oxidase has a specific activity in the range of about 10-12 Enzyme Units per mg protein.

20. A method as in claim 12 wherein adding an azide comprises:
adding an amount of sodium azide in the range of about $7 \times 10^{-5}$ mg azide ($N_3$)/Enzyme Unit to about 8 mg azide ($N_3$)/Enzyme Unit; and wherein
the alcohol oxidase has a specific activity in the range of about 10-12 Enzyme Units per mg protein.

21. A method as in claim 12 wherein adding an azide comprises:
adding an amount of sodium azide in the range of about $7 \times 10^{-4}$ mg azide ($N_3$)/Enzyme Unit to about $1.35 \times 10^{-2}$ mg azide ($N_3$)/Enzyme Unit; and wherein
the alcohol oxidase has a specific activity in the range of about 10-12 Enzyme Units per mg protein.

22. The method of claim 12 in which the red absorbing complex is separated from the preparation by the use of differential solubility using ammonium sulfate or polyethylene glycol.

23. The method of claim 12 in which the red absorbing complex is separated from the preparation by specific precipitation.

24. The method of claim 12 in which the red absorbing complex is separated from the preparation by column chromatography.

25. The method of claim 12 in which the red absorbing complex is separated from the preparation by preparative electrophoresis.

26. The method of claim 12 in which the red absorbing complex is separated from the preparation by preparative ultracentrifugation.

27. The method of claim 12 in which the red absorbing complex is separated from the preparation by dialysis to crystallization.

28. A method of determining the presence of active alcohol oxidase comprising:
observing the color of a composition of matter comprising an alcohol oxidase and an azide compound selected from the group of compounds having the formula $R''(N_3)_x$ wherein $R''$ is a metal atom, a hydrogen atom, or the ammonium radical, and $N_3$ is the moiety $$N=N=N$$

the azide compound being present in an amount effective to form a red absorbing combination with active alcohol oxidase.

* * * * *